United States Patent [19]

Okawa

[11] Patent Number: 5,686,641
[45] Date of Patent: Nov. 11, 1997

[54] METHOD FOR THE PREPARATION OF ORGANOPENTASILOXANES

[75] Inventor: Tadashi Okawa, Chiba Prefecture, Japan

[73] Assignee: Dow Corning Toray Silicone Co., Ltd., Tokyo, Japan

[21] Appl. No.: 782,437

[22] Filed: Jan. 15, 1997

[30] Foreign Application Priority Data

Jan. 31, 1996 [JP] Japan ................................. 8-037487
Apr. 4, 1996 [JP] Japan ................................. 8-108453

[51] Int. Cl.$^6$ ................... C07F 7/08; C07F 7/18; C07F 7/10
[52] U.S. Cl. ..................... 556/453; 556/425; 556/442
[58] Field of Search ........................... 556/453, 425, 556/442

[56] References Cited

U.S. PATENT DOCUMENTS

| | | | |
|---|---|---|---|
| 5,194,649 | 3/1993 | Okawa | 556/451 |
| 5,470,934 | 11/1995 | Saruyama et al. | 556/453 X |
| 5,527,935 | 6/1996 | Stepp et al. | 556/453 X |
| 5,605,997 | 2/1997 | Yamamoto et al. | 556/453 X |

*Primary Examiner*—Paul F. Shaver
*Attorney, Agent, or Firm*—Paula J. Lagattuta

[57] ABSTRACT

A method for the preparation of very pure organopentasiloxane having the hydrogen atom or an aliphatically unsaturated monovalent hydrocarbon group bonded to the silicon atom at one molecular chain terminal and having a hydrolyzable group or groups bonded to the silicon atom at the other molecular chain terminal.

5 Claims, No Drawings

METHOD FOR THE PREPARATION OF ORGANOPENTASILOXANES

BACKGROUND OF THE INVENTION

1. Field of the Invention

This invention relates to methods for the preparation of organopentasiloxanes. More particularly, this invention relates to a method for the preparation of very pure organopentasiloxane having a hydrogen atom or an aliphatically unsaturated monovalent hydrocarbon group bonded to a silicon atom at one molecular chain terminal and having a hydrolyzable group or groups bonded to a silicon atom at the other molecular chain terminal.

2. Description of the Related Art

The following organosilicon compounds are used as silane coupling agents and as precursors for the synthesis of reactive polyolefin resins: (i) organosilicon compounds bearing both the hydrogen atom and hydrolyzable groups bonded to silicon in each molecule and (ii) organosilicon compounds bearing both aliphatically unsaturated monovalent hydrocarbon and hydrolyzable groups bonded to silicon in each molecule. The former are exemplified by trimethoxysilane, methyldimethoxysilane, dimethylmethoxysilane, dimethylacetoxysilane, and so forth. The latter are exemplified by vinyltrimethoxysilane, vinyltriacetoxysilane, vinyltrioximesilane, hexenyltrimethoxysilane, hexenyltriacetoxysilane, and the like.

However, the hydrolyzable groups and aliphatically unsaturated monovalent hydrocarbon group (or hydrogen atom) are bonded to the same silicon atom in these organosilicon compounds. As a result, when these organosilicon compounds are used as silane coupling agents to treat the surface of inorganic filler or packing, the Si-bonded hydrogen or aliphatically unsaturated monovalent hydrocarbon group end up being masked in the interior of the crosslinked film afforded by hydrolysis and condensation, and the effect of the surface treatment will as a consequence be less than anticipated. In specific terms, an adequate fatigue resistance will not be obtained for silicon rubber afforded by curing a silicone rubber composition that contains inorganic filler whose surface has been treated with such an organosilicon compound. Moreover, when these organosilicon compounds are copolymerized with olefin in their role as a precursor for reactive polyolefin resin, their Si-bonded hydrogen or aliphatically unsaturated monovalent hydrocarbon group again end up masked within the resulting polyolefin resin and the reactivity of the corresponding polyolefin resin will again be less than expected.

The inventor has already proposed organopentasiloxane having a hydrogen atom or an aliphatically unsaturated monovalent hydrocarbon group bonded to a silicon atom at one molecular chain terminal and having a hydrolyzable group or groups bonded to the silicon atom at the other molecular chain terminal (see Japanese Patent Application Laid Open Number Hei 6-9657 (1994). This reference also discloses a method for the preparation of organopentasiloxanes that is characterized by ring-opening hexamethylcyclotrisiloxane with organohalosilane, hydrolyzing the 1-halo-organotetrasiloxane thus obtained to yield 1-hydroxy-organotetrasiloxane, and condensing the 1-halo-organotetrasiloxane with hydrolyzable silane.

With respect to this preparation of organopentasiloxane, the 1-halo-organotetrasiloxane is very hydrolyzable and its hydrolysis must therefore be run very carefully at low temperatures. In addition, the 1-hydroxy-organotetrasiloxane afforded by this hydrolysis has a strong tendency to dimerize by condensation and there is a strong tendency for the siloxane bonds in this system to rearrange. These factors operate to reduce the purity of the 1-hydroxy-organotetrasiloxane and substantially reduce the purity of the organopentasiloxane (hydrogen or aliphatically unsaturated monovalent hydrocarbon group bonded to the silicon at one molecular chain terminal and hydrolyzable group(s) bonded to the silicon at the other molecular chain terminal) afforded by the ensuing condensation with hydrolyzable silane. These problems make the method disclosed in Japanese Patent Application Laid Open (Kokai or Unexamined) Number Hei 6-9657 fairly unsuitable for the mass production of the subject organopentasiloxane.

The inventor achieved the present invention as a result of extensive research directed to solving the problems described above.

In specific terms, the object of the present invention is to provide a method for the preparation of very pure organopentasiloxane having a hydrogen atom or an aliphatically unsaturated monovalent hydrocarbon group bonded to a silicon atom at one molecular chain terminal and having a hydrolyzable group or groups bonded to a silicon atom at the other molecular chain terminal.

SUMMARY OF THE INVENTION

The present invention relates to a method for the preparation of an organopentasiloxanes having the general formula (IV):

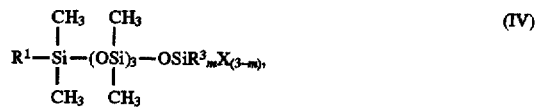

the method comprising the steps of:

A) hydrolyzing a compound selected from (i) 1-acyloxy-organotetrasiloxanes having the general formula (I):

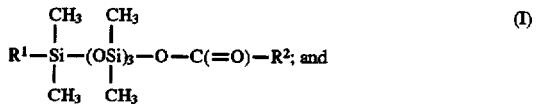

(ii) first organosiloxane oligomer mixtures having a main component (I); to prepare a compound selected from the group consisting of (a) 1-hydroxy-organotetrasiloxanes having the general formula (II):

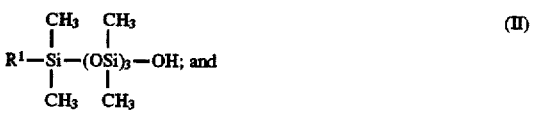

(b) second organosiloxane oligomer mixture having a main component (II); and (B) condensing the compound prepared in step (A) with a hydrolyzable silane having the general formula (III);

to yield an organopentasiloxane having the general formula (IV); wherein $R^1$ is a hydrogen atom or an aliphatically unsaturated monovalent hydrocarbon group, $R^2$ is a monovalent hydrocarbon group, $R^3$ is a monovalent hydrocarbon group, X is a hydrolyzable group, and n=0, 1, or 2.

DETAILED DESCRIPTION OF THE INVENTION

The method according to the present invention for the preparation of organopentasiloxane will be explained in detail in the following.

The preparative method according to the present invention begins with the preparation of a 1-hydroxy-organotetrasiloxane with general formula (II) or a first organosiloxane oligomer mixture whose main component is (II) by the hydrolysis of a 1-acyloxy-organotetrasiloxane with general formula (I) or a second organosiloxane oligomer mixture whose main component is (I). The organosiloxane oligomer mixture whose main component is (I) (hereinafter abbreviated as a (I)-based organosiloxane oligomer mixture) refers to a mixture of organosiloxane oligomers that have an acyloxy group bonded to the silicon atom at a molecular chain terminal as in general formula (I) but which have different numbers of siloxane units. The same principle applies with respect to the second organosiloxane oligomer mixture whose main component is a 1-hydroxy-organotetrasiloxane with general formula (II) (hereinafter abbreviated as a (II)-based organosiloxane oligomer mixture.) $R^1$ in general formula (I) is a hydrogen atom or an aliphatically unsaturated monovalent hydrocarbon group. The monovalent hydrocarbon groups encompassed by $R^1$ are specifically exemplified by alkenyl groups such as vinyl, allyl, isopropenyl, butenyl, pentenyl, hexenyl, and the like and by cycloalkenyl groups such as cyclohexenyl, norbornenyl, and the like. $R^2$ in general formula (I) represents monovalent hydrocarbon group, and it is specifically exemplified by alkyl groups such as methyl, ethyl, propyl, butyl, and pentyl; alkenyl groups such as vinyl, allyl, butenyl, and pentenyl; aryl groups such as phenyl, tolyl, and xylyl; and aralkyl groups such as benzyl and phenethyl. Methyl is specifically preferred for $R^2$.

The 1-acyloxy-organotetrasiloxane (I) can be prepared, for example, by the condensation of 1-halo-organotetrasiloxane with alkali metal acylate or by the ring-opening of hexamethylcyclotrisiloxane with acyloxysilane with general formula (V):

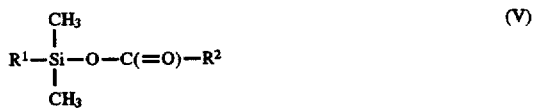

wherein $R^1$ is a hydrogen atom or an aliphatically unsaturated monovalent hydrocarbon group and $R^2$ is a monovalent hydrocarbon group (refer to Japanese Patent Publication Kokoku) Number Sho 43-9080 (1968) and *European Polymer Journal*, Volume 17, pp. 413–419, 1981). The condensation reaction between 1-halo-organotetrasiloxane and alkali metal acylate can be run at room temperature, but is preferably run with heating. This condensation reaction can be run without the use of solvent, but is preferably run in an organic solvent, such as toluene, xylene, etc., at the reflux temperature of the organic solvent. The alkali metal acylate is specifically exemplified by the sodium and potassium salts of carboxylic acids such as acetic acid, propionic acid, benzoic acid, acrylic acid, methacrylic acid, cinnamic acid, and the like. Sodium acetate and potassium acetate are preferred alkali metal acylates. The alkali metal acylate is preferably used in this condensation reaction in at least an equimolar quantity and particularly preferably in a 1- to 1.5-fold molar quantity, in each case relative to the 1-halo-organotetrasiloxane. In the case of ring-opening of hexamethylcyclotrisiloxane by the acyloxysilane (V), this ring-opening reaction is preferably accelerated by the addition of a Lewis acid, e.g., zinc chloride, boron trifluoride, aluminum chloride, etc., or a protic acid such as hydrochloric acid, sulfuric acid, trifluoroacetic acid, trifluoromethanesulfonic acid, etc. $R^1$ (V) is a hydrogen atom or an aliphatically unsaturated monovalent hydrocarbon group, and the monovalent hydrocarbon groups encompassed by $R^1$ are specifically exemplified by the same monovalent hydrocarbon groups as provided above. $R^2$ in (V) is a monovalent hydrocarbon group, and it is again specifically exemplified by the same monovalent hydrocarbon groups as provided above. The acyloxysilane is preferably used in this ring-opening reaction in at least an equimolar quantity and particularly preferably in a 1- to 1.5-fold molar quantity, in each case relative to the hexamethylcyclotrisiloxane. This ring-opening reaction can be run in the absence of solvent or may be run in an organic solvent such as toluene, xylene, etc.

After its preparation, the 1-acyloxy-organotetrasiloxane (I) or (I)-based organosiloxane oligomer mixture is hydrolyzed to give a 1-hydroxy-organotetrasiloxane with general formula (II) or a (II)-based organosiloxane oligomer mixture. This hydrolysis of 1-acyloxy-organotetrasiloxane (I) must be run carefully in order to prevent dimerization of the 1-hydroxy-organotetrasiloxane (II) afforded by hydrolysis and inhibit siloxane bond rearrangement; however, this hydrolysis can be run under milder conditions than heretofore used for the hydrolysis of 1-halo-organotetrasiloxane. The hydrolysis of the 1-acyloxy-organotetrasiloxane (I) is preferably carried out in the presence of an alkali metal carbonate or alkaline-earth metal carbonate. The alkali metal carbonates are exemplified by sodium bicarbonate, sodium carbonate, potassium carbonate, and lithium carbonate, and the alkaline-earth metal carbonates are specifically exemplified by magnesium carbonate, calcium carbonate, and barium carbonate. The alkali metal or alkaline-earth metal carbonate is preferably added at 0.5 to 1.5 moles per 1 mole 1-acyloxy-organotetrasiloxane (I). An amine compound is preferably added as hydrolysis catalyst in order to accelerate hydrolysis, and this amine compound is exemplified by triethylamine, pyridine, piperidine, quinoline, and diethylhydroxylamine. The amine compound is preferably added at from 0.0001 to 1 mole per 1 mole 1-acyloxy-organotetrasiloxane (I). This hydrolysis can be run in the absence of organic solvent, but may also be run in organic solvent, for example, aromatic hydrocarbons such as toluene, xylene, etc.; ethers such as diethyl ether, tetrahydrofuran, etc.; and chlorinated hydrocarbons such as chloroform, carbon tetrachloride, methylene chloride, etc. The hydrolysis reaction temperature is preferably from −10° C. to 100° C. and particularly preferably from 0° C. to 50° C.

The organopentasiloxane (IV) or organosiloxane oligomer mixture whose main component is (IV) is then prepared by condensing hydrolyzable silane with general formula (III) with the 1-hydroxy-organotetrasiloxane (II) or (II)-based organosiloxane oligomer mixture afforded by hydrolysis of the 1-acyloxy-organotetrasiloxane (I) or (I)-based organosiloxane oligomer mixture. An organosiloxane oligomer mixture whose main component is organopentasiloxane (IV) (hereinafter abbreviated as a (IV)-based organosiloxane oligomer mixture) refers to a mixture of organosiloxane oligomers that have a hydrolyzable group or groups bonded to silicon at the molecular chain terminal as in general formula (IV) but which have different numbers of siloxane units. The X in general formula (III) is a silicon-bonded hydrolyzable group and is specifically exemplified by alkoxy groups such as methoxy, ethoxy, propoxy, butoxy, pentyloxy, hexyloxy, and so forth; alkenyloxy groups such as vinyloxy, allyloxy, butenyloxy, hexenyloxy, isopropenyloxy, and so forth; aryloxy groups such as phenyloxy, tolyloxy, xylyloxy, and so forth; arylalkoxy groups such as benzyloxy, phenethyloxy, and so forth; acyloxy groups such as acetoxy, propionyloxy, benzoyloxy, and so forth; aminoxy; and halogen atoms such as chlorine, bromine, and iodine. Alkoxy and acyloxy groups are preferred. The subscript n in general formula (III) is 0, 1, or 2. The organopentasiloxane product is trifunctional when hydrolyzable silane with n=0 is used, difunctional when hydrolyzable silane with n=1 is used, and monofunctional when hydrolyzable silane with n=2 is used.

The condensation reaction can be accelerated by heating the mixture of hydrolyzable silane (III) and 1-hydroxy-organotetrasiloxane (II) or (II)-based organosiloxane oligomer mixture. A condensation reaction catalyst can also be added in order to accelerate the condensation reaction. Said condensation reaction catalysts are specifically exemplified by carboxylic acids such as acetic acid, propionic acid, acrylic acid, and so forth; inorganic acids such as carbonic acid, hydrochloric acid, sulfuric acid, and so forth; inorganic bases such as sodium hydroxide, potassium hydroxide, lithium hydroxide, calcium hydroxide, magnesium hydroxide, and so forth; and amines such as triethylamine, pyridine, piperidine, quinoline, diethylhydroxylamine, and so forth. The hydrolyzable silane (III) is preferably added in at least an equimolar quantity and particularly preferably in a 1- to 1.5-fold molar quantity, in each case relative to the 1-hydroxy-organotetrasiloxane (II). The condensation reaction temperature is preferably from 70° C. to 130° C.: the condensation reaction will not develop rapidly at a reaction temperature below 70° C., while temperatures higher than 130° C. facilitate siloxane bond rearrangement in the organopentasiloxane product. The described condensation reaction between hydrolyzable silane (III) and the 1-hydroxy-organotetrasiloxane (II) or (III)-based organosiloxane oligomer mixture affords a very pure organopentasiloxane (IV). In addition, while the organopentasiloxane (IV) is obtained as an organosiloxane oligomer mixture whose main component is (V), this can as necessary be purified by distillation.

The organopentasiloxane (IV) prepared as described above carries the hydrogen atom or an aliphatically unsaturated monovalent hydrocarbon group on the silicon atom at one molecular chain terminal and carries a hydrolyzable group or groups on the silicon atom at the other molecular chain terminal. This particular structure permits organopentasiloxane (IV) to be used as a silane coupling agent or starting material for the preparation of reactive polyolefin resin. Reinforcing inorganic filler whose surface has been treated with (IV) can impart an excellent fatigue resistance to silicone rubbers.

EXAMPLES

The method according to the present invention for the preparation of organopentasiloxane will be explained with reference to working examples.

EXAMPLE 1

421.8 g (3.5 moles) dimethylvinylchlorosilane, 778.8 g (3.5 moles) hexamethylcyclotrisiloxane, 23.8 g N,N-dimethylformamide, and 238 g acetonitrile were introduced into a four-neck flask equipped with a stirrer, and the system was stirred for 3 hours at room temperature. The low-boiling components were then distilled out by heating the system to 100° C. at 20 mmHg to leave 1,073 g of a liquid. Analysis of an aliquot of this liquid by gas chromatography (GLC), infrared absorption (IR), nuclear magnetic resonance (NMR), and gas chromatography-mass spectrometry (GC-MS) confirmed it to be an organosiloxane oligomer mixture whose main component was 1-chloro-7-vinyl-octamethyltetrasiloxane (the GLC purity of this siloxane in the organosiloxane mixture was 59.1 weight %) with the following formula.

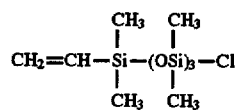

255.6 g (3.12 moles) sodium acetate and 300 mL toluene were then introduced into another four-neck flask equipped with a water separation tube, stirrer, and Dimroth condenser and this system was azeotropically dried by stirring for 30 minutes while heating at the reflux temperature of toluene. The entire amount of the above-described organosiloxane oligomer mixture was then added dropwise to the system and the system was stirred for 15 minutes while heating at 90° C. GLC analysis of an aliquot of the reaction mixture at this point showed that the 1-chloro-7-vinyl-octamethyltetrasiloxane peak had disappeared. The sodium chloride by-product and unreacted sodium acetate were subsequently filtered off to give a toluene solution. A sample was taken from the toluene solution and freed of the toluene and analyzed by GLC, IR, NMR, and GC-MS. These analyses confirmed it to be a toluene solution of an organosiloxane oligomer mixture whose main component was 1-acetoxy-7-vinyl-octamethyltetrasiloxane (the GLC purity of this siloxane in the toluene solution was 46.1 weight %) with the following formula

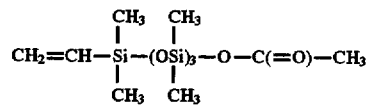

550 mL water, 240 g (2.86 moles) sodium bicarbonate, ad 13.1 g (0.13 mole) triethylamine were added to the entire amount of the above-described toluene solution of mixed organosiloxane oligomers and the system was then stirred at room temperature for 5 hours. Analysis of an aliquot of the reaction mixture at this point by GLC showed that the peak for 1-acetoxy-7-vinyl-octamethyltetrasiloxane had disappeared. The water was subsequently removed from the system and the resulting toluene solution was washed twice with water. The toluene solution was thereafter heated in an evaporator at reduced pressure in order to distill out the toluene. Analysis of an aliquot of the resulting liquid by GLC, IR, NRM, and GC-MS confirmed it to be an organosiloxane oligomer mixture whose main component was 1-hydroxy-7-vinyl-octamethyltetrasiloxane (the GLC purity of this siloxane in the organosiloxane oligomer mixture was 53.5 weight %) with the following formula.

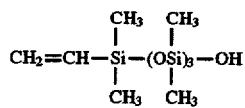

The entire amount of this organosiloxane oligomer mixture was combined with 434.2 g (2.86 moles) tetramethoxysilane and 1.5 calcium hydroxide and the system was stirred for 3 hours while heating at the reflux temperature of tetramthoxysilane. The calcium hydroxide was then filtered from the system and the filtrate was distilled under reduced pressure to yield 386 g (overall yield=25 weight %) of a fraction at 95°–99° C./1 mm/Hg. Analysis of an aliquot of this fraction by GLC, IR, NMR, and GC-MS confirmed it to be an organosiloxane oligomer mixture composed of 94.5 weight % 1,1,1-trimethoxy-9-vinyl-octamethylpentasiloxane with the formula

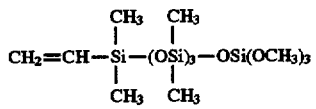

3.3 weight % 1,9-divinyl-decamethylpentasiloxane with the formula

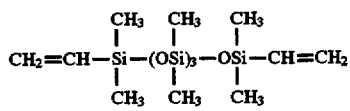

and 2.2 weight % other components.

EXAMPLE 2

59.9 g (0.73 mole) sodium acetate and 50 g toluene were placed in a stirrer-equipped four-neck flask and the system was azeotropically dried by stirring for 30 minutes while heating at the reflux temperature of toluene. 80 g (0.66 mole) dimethylvinylchlorosilane was then added to the system dropwise. After the completion of addition the system was heated and stirred for 10 minutes at 110° C. GLC analysis of an aliquot of the reaction mixture at this point confirmed the disappearance of the dimethylvinylchlorosilane peak. The sodium chloride by-product and unreacted sodium acetate were then filtered off to yield a toluene solution. A sample was taken from the toluene solution and freed of the toluene and analyzed by GLC, IR, NMR, and GC-MS. These analyses confirmed this to be a toluene solution of dimethylvinylacetoxysilane (the GLC purity of this silane in the toluene solution was 59.1 weight %).

To this entire toluene solution of dimethylvinylacetoxysilane were added 147.4 g (0.66 mole) hexamethylcyclotrisiloxane and 2.43 g zinc chloride and the system was heated while stirring at 110° C. to 125° C. for 11 hours. GLC analysis of an aliquot of the reaction mixture at this point showed the dimethylvinylacetoxysilane conversion to organosiloxane oligomer (reaction ratio) to be 85%. The zinc chloride was then filtered from this system to yield a toluene solution. A sample was taken from this toluene solution and freed of the toluene and analyzed by GLC, IR, NMR, and GC-MS. These analyses confirmed it to be a toluene solution of an organosiloxane oligomer mixture whose main component was 1-acetoxy-7-vinyl-octamethyltetrasiloxane (the GLC purity of this siloxane in the toluene solution was 39.5 weight %) with the following formula.

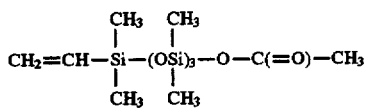

200 mL water, 61.3 g (0.73 mole) sodium bicarbonate, and 4.1 g (40.6 mmole) triethylamine were added to the entire amount of the above-described toluene solution of mixed organosiloxane oligomers and the system was then stirred at room temperature for 5 hours. Analysis of an aliquot of the reaction mixture at this point by GLC showed that the peak for 1-acetoxy-7-vinyl-octamethyltetrasiloxane had disappeared. The water was subsequently removed from the system and the resulting toluene solution was washed twice with water. The toluene solution was thereafter heated in an evaporator at reduced pressure in order to distill out the toluene. Analysis of an aliquot of the resulting liquid by GLC, IR, NMR, and GC-MS confirmed it to be an organosiloxane oligomer mixture whose main component was 1-hydroxy-7-vinyl-octamethyltetrasiloxane (the GLC purity of this siloxane in the organosiloxane oligomer mixture was 73.2 weight %) with the following formula.

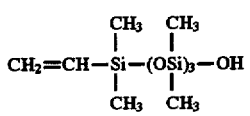

The entire amount of this organosiloxane oligomer mixture was combined with 122.2 g (0.80 mole) tetramethoxysilane and 0.43 calcium hydroxide and the system was stirred for 1 hour while heating at the reflex temperature of tetramethoxysilane. The calcium hydroxide was then filtered from the system and the filtrate was distilled under reduced pressure to yield 115 g (overall yield=39 weight %) of a fraction at 91°–95° C./1 mmHg. Analysis of an aliquot of this fraction by GLC, IR, NMR, and GC-MS confirmed it to be an organosiloxane oligomer mixture composed of 96.6 weight % 1,1,1-trimethoxy-9-vinyl-octamethylpentasiloxane with the formula

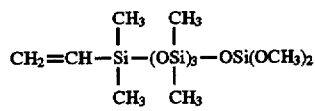

0.4 weight % 1,9-divinyl-decamethylpentasiloxane with the formula

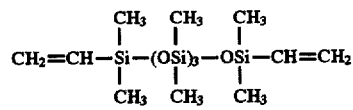

and 3.0 weight % other components.

EXAMPLE 3

An organosiloxane oligomer mixture whose main component was 1-hydroxy-7-vinyl-octamethyltetrasiloxane (the GLC purity of this siloxane in the organosiloxane oligomer mixture was 73.2 weight %) with the formula

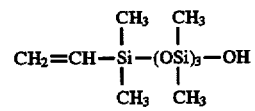

was prepared as in Example 2. 332.8 g (1.6 moles) dimethyldiacetoxysilane and 89.0 g (0.88 mole) triethylamine were added to the entire amount of this organosiloxane oligomer mixture and the system was heated at 80° C. while stirring for 3 hours. GLC analysis of the reaction mixture at this point confirmed the dissappearance of the 1-hydroxy-7-vinyl-octamethyltetrasiloxane peak. The system was subsequently heated under reduced pressure in order to distill off the low boilers and leave 150 g of a liquid. Analysis of an aliquot of this liquid by GLC, IR, NMR, and GC-MS confirmed it to be an organosiloxane oligomer mixture whose main component was 1-acetoxy-9-vinyl-decamethylpentasiloxane (the GLC purity of this siloxane in the organosiloxane oligomer mixture was 96 weight %) with the following formula.

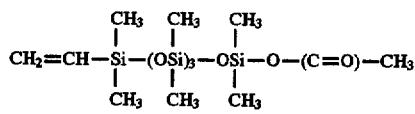

COMPARATIVE EXAMPLE 1

1,153.7 g (9.6 moles) dimethylvinylchlorosilane, 2,130 g (9.6 moles) hexamethylcyclotrisiloxane, 65.1 g N,N-dimethylformamide, and 651 g acetonitrile were introduced into a stirrer-equipped four-neck flask and the system was stirred for 5 hours at room temperature. Subsequent heating to 90° C. at a reduced pressure of 20 mmHg in order to distill out the low boilers yielded 3,100 g of a liquid. Analysis of an aliquot of this liquid by GLC, IR, NMR, and GC-MS confirmed it to be an organosiloxane oligomer mixture whose main component was 1-chloro-7-vinyl-octamethyltetrasiloxane (the GLC purity of this siloxane in the organosiloxane oligomer mixture was 49.8 weight %) with the following formula.

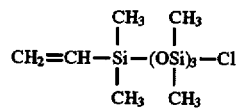

4,000 mL water, 200 Ml toluene, and 1,100 g (13.14 moles) sodium bicarbonate were introduced into another stirrer-equipped four-neck flask. While stirring this system, the toluene solution consisting of the entire amount of the aforementioned organosiloxane oligomer mixture dissolved in 800 mL toluene was added dropwise from and addition funnel. After the completion of addition the water was removed from the system and the resulting toluene solution was washed twice with water. A sample was taken from this toluene solution and freed of the toluene and analyzed by GLC, IR, NMR, and GC-MS. These analyses showed that about 43 weight % 1-hydroxy-7-vinyl-octamethyltetrasiloxane with the formula

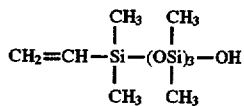

had condensed and dimerized into 1,4-divinyl-hexadecamethyloctasiloxane with the following formula.

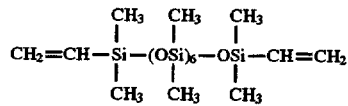

Its siloxane bond rearrangement with the production of 1,9-divinyl-decamethylpentasiloxane with the formula

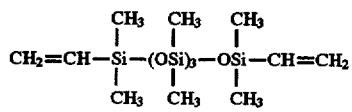

was also confirmed. The toluene solution was heated in an evaporator under reduced pressure to distill out the toluene and give 4,246 g of a liquid.

There were added 1,176 g (7.7 moles) tetramethoxysilane and 7.05 g calcium hydroxide to 2,173 g of the aforementioned liquid, and this system was stirred for 9 hours while heating at the reflux temperature of tetramethoxysilane. The calcium hydroxide was then filtered from the system and the filtrate afforded thereby was distilled under reduced pressure to give 150 g of a fraction at 89.5° C. to 90° C./1 mmHg. Analysis of an aliquot of this fraction by GLC, IR, NMR, and GC-MS showed that it was an organosiloxane oligomer mixture composed of 80.6 weight % 1,1,1-trimethoxy-9-vinyl-octamethylpentasiloxane with the formula

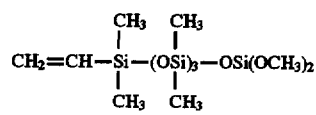

10.1 weight % 1,9-divinyl-decamethylpentasiloxane with the formula

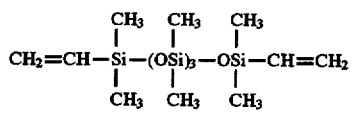

and 9.3 weight % other components. The reasons for the low purity of this 1,1,1-trimethoxy-9-vinyl-octamethylpentasiloxane were presumed to be dimerization by condensation during hydrolysis and associated siloxane bond rearrangement.

EXAMPLE 4

57.2 g (0.70 mole) sodium acetate and 45 g toluene were placed in a stirrer-equipped four-neck flask and the system was azeotropically dried by stirring for 30 minutes while heating at the reflux temperature of toluene. 62.7 g (0.66 mole) dimethylchlorosilane was then added to the system dropwise. After the completion of addition the system was heated and stirred for 15 minutes at 90° C. GLC analysis of an aliquot of the reaction mixture at this point confirmed the disappearance of the dimethylchlorosilane peak. The sodium chloride by-product and unreacted sodium acetate were then filtered off to yield a toluene solution. A sample was taken from the toluene solution and freed of the toluene and analyzed by GLC, IR, NMR, and GC-MS. These analyses confirmed this to be toluene solution of dimethylacetoxysilane (the GLC purity of this silane in the toluene solution was 57.9 weight %).

To this entire toluene solution of dimethylacetoxysilane were added 147.4 g (0.66 mole) hexamethylcyclotrisiloxane and 0.4 g (2.7 mmol) trifluoromethanesulfonic acid and the system was stirred at 30° C. for 5.5 hours. GLC analysis of an aliquot of the reaction mixture at this point showed the dimethylacetoxysilane conversion to organosiloxane oligomer (reaction ratio) to be 92%. The trifluoromethanesulfonic acid in the system was then neutralized by the addition of 0.6 g (4.0 mmol) hexamethyldisilazane and the ammonium trifluoromethanesulfonate by-product was removed from the system by decanting to yield a toluene solution. A sample was taken from this toluene solution and freed of the toluene and analyzed by GLC, IR, NMR, and GC-MS. These analyses confirmed it to be a toluene solution of an organosiloxane oligomer mixture whose main component was 1-acetoxy-octamethyltetrasiloxane (the GLC purity of this siloxane in the toluene solution was 49.4 weight %) with the following formula.

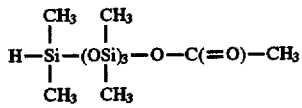

150 mL water, 50.2 g (0.6 mole) sodium bicarbonate, and 3.0 g (29.9 mmole) triethylamine were added to the entire amount of the above-described toluene solution of mixed organosiloxane oligomers and the system was then stirred at room temperature for 4 hours. Analysis of the system at this point by GLC showed that the peak for 1-acetoxy-octamethyltetrasiloxane had disappeared. The water was subsequently removed from the system and the resulting toluene solution was washed twice with water. The toluene solution was thereafter heated in an evaporator at reduced pressure in order to distill out the toluene. Analysis of an aliquot of the resulting liquid by GLC, IR, NMR, and GC-MS confirmed it to be an organosiloxane oligomer mixture whose main component was 1-hydroxy-octamethyltetrasiloxane (the GLC purity of this siloxane in the organosiloxane oligomer mixture was 78.1 weight %) with the following formula.

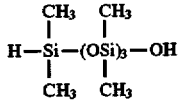

The entire amount of this organosiloxane oligomer mixture was combined with 81.7 g (0.54 mole) tetramethoxysilane and 0.32 g calcium hydroxide and the system was stirred for 10 minutes while heating at the reflux temperature of tetramethoxysilane. The calcium hydroxide was then filtered from the system and the filtrate was distilled under reduced pressure to yield 122 g (overall yield=44 weight %) of a fraction at 80°–87° C./1 mmHg. Analysis of an aliquot of this fraction by GLC, IR, NMR, and GC-MS confirmed it to be an organosiloxane oligomer mixture composed of 96.3 weight % 1,1,1-trimethoxy-octamethylpentasiloxane with the formula

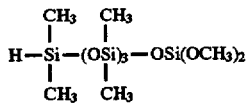

and 3.7 weight % other components.

EXAMPLE 5

47.3 g (0.5 mole) dimethyldichlorosilane, 111.3 g (0.5 mole) hexamethylcyclotrisiloxane, 3.4 g N,N-dimethylformamide, and 34 g acetonitrile were introduced into a four-neck flask equipped with a stirrer, and the system was stirred for 1 hour at room temperature. The low-boiling components were then distilled out by heating the system to 80° C. at 20 mmHg to leave a liquid. Analysis of an aliquot of this liquid by GLC, IR, NMR, and GC-MS confirmed it to be an organosiloxane oligomer mixture whose main component was 1-chloro-octamethyltetrasiloxane (the GLC purity of this siloxane in the organosiloxane oligomer mixture was 86 weight %) with the following formula.

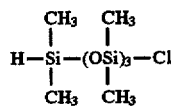

46.2 g (0.55 mole) sodium acetate and 200 mL toluene were then introduced into another four-neck flask equipped with a water separation tube, stirrer, and Dimroth condenser and this system was azeotropically dried by stirring for 30 minutes while heating at the reflux temperature of toluene. The entire amount of the above-described organosiloxane oligomer mixture was then added dropwise to the system and the system was stirred for 5 minutes while heating at 95° C. GLC analysis of an aliquot of the reaction mixture at this point showed that the 1-chloro-octamethyltetrasiloxane peak had disappeared. The sodium chloride by-product and unreacted sodium acetate were subsequently filtered off to give a toluene solution. A portion of this toluene solution was taken and this toluene solution was heated under reduced pressure to yield 108 g of a fraction at 64°–67° C./1 mmHg. Analysis of an aliquot of this fraction confirmed it to be an organosiloxane oligomer mixture of 98.6 weight % 1-acetoxy-octamethyltetrasiloxane with the following formula

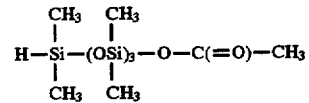

and 1.4 weight % other components.

450 mL water, 46.2 g (0.55 mol) sodium bicarbonate, and 2.5 g (25 mmol) triethylamine were added to the entire amount of the above-described organosiloxane oligomer mixture dissolved in 100 mL toluene and the system was then stirred at room temperature for 4 hours. Analysis of an aliquot of the reaction mixture at this point by GLC showed the peak for 1-acetoxy-octamethyltetrasiloxane had disappeared. The water was subsequently removed from the system and the resulting toluene solution was washed twice with water. The toluene solution was thereafter heated in an evaporator at reduced pressure in order to distill out the toluene. Analysis of an aliquot of the resulting liquid by GLC, IR, NMR, and GC-MS confirmed it to be an organosiloxane oligomer mixture whose main component was 1-hydroxy-octamethyltetrasiloxane (the GLC purity of this siloxane in the organosiloxane oligomer mixture was 88.0 weight %) with the following formula.

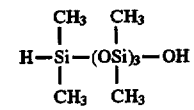

The entire amount of this organosiloxane oligomer mixture was combined with 83.6 g (0.55 mole) tetramethoxysilane and 2.2 g calcium hydroxide and the system was stirred for 7 hours while heating at the reflux temperature of tetramethoxysilane. The calcium hydroxide was then filtered from the system and the filtrate was distilled under reduced pressure to yield 102 g (overall yield=49 weight %) of a fraction at 92°–96° C./2 mmHg. Analysis of an aliquot of this fraction by GLC, IR, NMR, and GC-MS confirmed it to be an organosiloxane oligomer mixture composed of 99.2 weight %, 1,1,1-trimethoxy-octamethylpentasiloxane with the formula

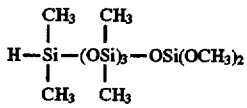

and 0.8 weight % other components.

The preparative method according to the present invention characteristically yields a very pure organopentasiloxane having the hydrogen atom or an aliphatically unsaturated monovalent hydrocarbon group bonded to the silicon atom at one molecular chain terminal and a hydrolyzable group or groups bonded to the siloxane atom at the other molecular chain terminal.

That which is claimed is:

1. A method for preparing an organopentasiloxane having the general formula (IV):

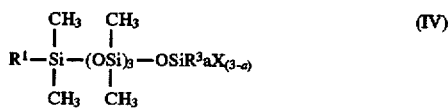 (IV)

the method comprising the steps of:

A) hydrolyzing a compound selected from the group consisting of a 1-acyloxy-organotetrasiloxane having the with general formula (I):

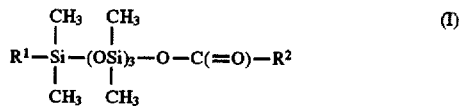 (I)

and first organosiloxane oligomer mixtures having a main component having the general formula (I) to produce a compound selected from the group consisting of 1-hydroxy-organotetrasiloxanes having the general formula (II):

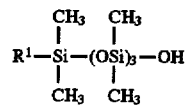

and second organosiloxane oligomer mixtures having a main component is (II); and B) condensing the compound produced in step (A) with a hydrolyzable silane having the general formula (III):

 (III)

wherein wherein $R^1$ is a hydrogen atom or an aliphatically unsaturated monovalent hydrocarbon group, $R^2$ is a monovalent hydrocarbon group, $R^3$ is a monovalent hydrocarbon group, X is a hydrolyzable group, and $\underline{n}$=0, 1, or 2.

2. The method according to claim 1, wherein the 1-acyloxy-organotetrasiloxane having general formula (I) is prepared by ring-opening of hexamethylcyclotrisiloxane with an acyloxysilane having general formula (V)

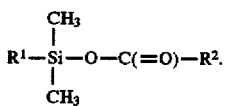

3. The method according to claim 1, wherein X is alkoxy or acyloxy.

4. The method according to claim 1, wherein $R^1$ is a hydrogen atom.

5. The method according to claim 1, wherein $R^1$ is an aliphatically unsaturated monovalent hydrocarbon group.

* * * * *